United States Patent [19]
Peithman

[11] Patent Number: 6,132,211
[45] Date of Patent: *Oct. 17, 2000

[54] PORTABLE DENTAL CAMERA, SYSTEM AND METHOD

[75] Inventor: Keith C. Peithman, York, Pa.

[73] Assignee: Dentsply International Inc.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/003,132

[22] Filed: Jan. 6, 1998

Related U.S. Application Data

[63] Continuation of application No. 08/900,713, Jul. 25, 1997, Pat. No. 5,836,762, which is a continuation of application No. 08/541,564, Sep. 29, 1995, abandoned, which is a division of application No. 08/134,158, Oct. 8, 1993, Pat. No. 5,487,661.

[51] Int. Cl.⁷ ...................................................... A61C 1/00

[52] U.S. Cl. .............................................. 433/29; 600/121

[58] Field of Search .................................. 433/29, 31, 77, 433/116; 600/102, 109, 112, 121, 122, 125, 133

[56] References Cited

U.S. PATENT DOCUMENTS

| | | | |
|---|---|---|---|
| 3,794,091 | 2/1974 | Ersek et al. | 150/52 R |
| 3,809,072 | 5/1974 | Ersek et al. | 128/23 |
| 3,866,601 | 2/1975 | Russell | 128/4 |
| 4,132,227 | 1/1979 | Ibe | 128/4 |
| 4,184,175 | 1/1980 | Mullane, Jr. | 358/93 |
| 4,201,199 | 5/1980 | Smith | 128/7 |
| 4,234,306 | 11/1980 | Hamada et al. | 433/55 |
| 4,254,762 | 3/1981 | Yoon | 128/4 |
| 4,324,546 | 4/1982 | Heitlinger et al. | 433/25 |
| 4,327,735 | 5/1982 | Hampson | 128/348 |
| 4,468,197 | 8/1984 | Provost | 433/30 |
| 4,646,722 | 3/1987 | Silverstein et al. | 128/4 |
| 4,721,097 | 1/1988 | D'Almelio | 128/4 |
| 4,727,416 | 2/1988 | Cooper et al. | 358/98 |
| 4,741,326 | 5/1988 | Sidall et al. | 128/4 |
| 4,757,381 | 7/1988 | Cooper et al. | 358/98 |
| 4,772,275 | 9/1988 | Erlich | 604/280 |

(List continued on next page.)

FOREIGN PATENT DOCUMENTS 1405025   9/1975   United Kingdom.

OTHER PUBLICATIONS

Focusing on Your Future, AcuCam™ (6 pages).
Mandatory Sterilization, Dentistry Today May 1992 (1 page).
Dentsply/Equipment Division, Perspective™ Dental Imaging System . . . the one you've been waiting for., Discover Simplicity and Affordability.

(List continued on next page.)

Primary Examiner—John J. Wilson
Attorney, Agent, or Firm—Dale R. Lovercheck; James B. Bieber

[57]                ABSTRACT

The invention provides a camera system including a handpiece having a lens, and a cable connector connected to opposite ends of a cable and a plurality of power source bases. The cable connector includes a video processor. Each power source base has a base connector and a light source. The cable connector is adapted to be connected to each base connector. The camera system is used by connecting the cable connector one at a time to each of the base connectors. The handpiece is enclosed by a disposable sleeve. The sleeve is held against the handpiece by an autoclavable rigid jacket. The portable dental camera is maintain sterile by enclosing at least the distal end of the handpiece with a first sleeve, and generating an image of first patient with the camera and a first power source base in a first dental operatory room. The first sleeve is then removed from the handpiece and replaced with a second sleeve. An image of a second patient is then generated using the camera and a second power source base in a second dental operatory room. Preferably a sleeve which has a lens and is sterilizable and reusable is used to enclose the handpiece.

12 Claims, 3 Drawing Sheets

U.S. PATENT DOCUMENTS

| | | | |
|---|---|---|---|
| 4,797,101 | 1/1989 | Morris | 433/229 |
| 4,829,548 | 5/1989 | Halm et al. | 378/38 |
| 4,836,778 | 6/1989 | Baumrind et al. | 433/69 |
| 4,837,732 | 6/1989 | Brandestini et al. | 364/413.28 |
| 4,858,001 | 8/1989 | Milbank et al. | 358/98 |
| 4,878,485 | 11/1989 | Adair | 128/6 |
| 4,915,626 | 4/1990 | Lemmey | 433/31 |
| 4,947,245 | 8/1990 | Ogawa et al. | 358/98 |
| 4,952,149 | 8/1990 | Duret et al. | 433/215 |
| 4,956,859 | 9/1990 | Lanza et al. | 378/157 |
| 4,974,580 | 12/1990 | Anapliotis | 128/4 |
| 4,987,433 | 1/1991 | Gandrud | 354/132 |
| 4,994,910 | 2/1991 | Williams | 358/98 |
| 5,005,195 | 4/1991 | Lanza et al. | 378/62 |
| 5,005,196 | 4/1991 | Lanza et al. | 378/207 |
| 5,016,098 | 5/1991 | Cooper et al. | 358/98 |
| 5,016,643 | 5/1991 | Applegate et al. | 128/745 |
| 5,027,138 | 6/1991 | Gandrud | 354/62 |
| 5,049,070 | 9/1991 | Ademovic | 433/29 |
| 5,051,823 | 9/1991 | Cooper et al. | 358/98 |
| 5,052,924 | 10/1991 | Berg | 433/29 |
| 5,079,629 | 1/1992 | Oz | 358/100 |
| 5,090,040 | 2/1992 | Lanza et al. | 378/62 |
| 5,115,307 | 5/1992 | Cooper et al. | 358/98 |
| 5,178,536 | 1/1993 | Werly et al. | 433/29 |
| 5,196,702 | 3/1993 | Tsuji et al. | 250/327.2 |
| 5,224,049 | 6/1993 | Mushabac | 364/474.05 |
| 5,230,621 | 7/1993 | Jacoby | 433/29 |
| 5,234,802 | 8/1993 | Nakamura et al. | 430/403 |
| 5,251,025 | 10/1993 | Cooper et al. | 358/98 |
| 5,836,762 | 11/1998 | Peithman | 433/29 |

OTHER PUBLICATIONS

Dr. Gordon Christensen: "Intraoral video systems change practices", Patterson Today, Spring/Summer 1991, Special Report, p. 3.

Fuji Optical Systems, Inc., The Results are In! (1 page).

DentaCam, Images, the Science of Dental Imaging, Jul. 1990 vol. 1 No. 1 (8 pages).

Fuji Optical Systems, Inc., Now the Best Is Available For Everyone (11 pages).

Frink Dental Supply Co., IntraView Intraoral Camera System (2 pages).

Pro–Den Systems, ProScope™ Intra–Oral Video System (2 pages).

Levin, Practice Productivity, Seeing is Believing, Intraoral Imaging Spurs A Desire For Dental Treatment (1 page).

Pro–Den Systems, ProScope™, Intra–Oral Video Camera System, Factsheet (1 page).

Randle, Dear Doctor, New Image Industries Inc. (5 pages).

Gurevitch, Dear Doctor, New Image Industries. Apr. 17, 1992 (3 pages).

New Image Industries Inc., Focus on the Future Feb. 1992 (p. 101).

Dental Products Report, IntraView™ Intraoral Camera System . . . , Dental Products Report, p. 6.

New Image Industries Inc., AcuCam™, Focus On The Future, Intraoral Video Camera System (1 page).

AcuCam intraoral cameral system, Dental Products Report, New Products (pp. 48–49 and p. 54A; Apr. 1992).

Fuji Optical Systems, Inc., Patterson Dental Company, Other Intra–Oral Video Cameras Leave A Lot to Your Imagination (1 page).

Fuji Optical Systems, Inc., Vision Plus™—The Ultimate Cosmetic Imaging System (1 page).

Fuji Optical Systems, Inc., Great Products. (1 page).

Fuji Optical Systems, Inc., Fairy Tale: All Intra–Oral Video Cameras Are Alike (3 pages).

Dentsply/Equipment Division, Get a whole new Perspective on Dental Imaging, (6 pages).

Intraoral Camera Comparison (1 page).

Pro/Vision—DIS, Portable imaging system, Dental Products Report, Feb. 1992, pp. 146–148.

Code, Inc., Dentvision (1 page).

Dentistry Today, Tiny Still Video Camera . . . vol. 10 No. 7, Sep. 1991, (2 pages).

Henry Schein Inc., Still Video Imaging System by Panasonic, (1 page).

Dental Products Report, Intraoral Video and Computer Imaging . . . (pp. 18, 19, 42 and 44).

Dentistry Today, Feb. 1992, High–Tech Practice Management (4 pages).

PORTABLE DENTAL CAMERA, SYSTEM AND METHOD

This application is a continuation of application Ser. No. 08/900,713, filed Jul. 25, 1997; now U.S. Pat. No. 5,836,762, which is a continuation of patent application Ser. No. 08/541,564 filed Sep. 29, 1995, now abandoned which is a division of patent application Ser. No. 08/134,158, now U.S. Pat. No. 5,487,661.

The invention relates to a portable dental camera, system and a method. The invention provides a portable camera having a detachable lens housing and disposable handpiece sleeve useful in a system and method of periodic connection to each of a plurality of power and light sources. Use of a single portable camera with at least two power and light sources in different dental-operatory rooms in accordance with the invention substantially reduces the cost of dental image production. The use of disposable sleeves to protect the handpiece from contamination substantially reduces or eliminates the need for sterilization of the handpiece in accordance with the invention.

BACKGROUND OF THE INVENTION

A portable laparoscope camera having a readily detachable connector with a video processor for use with a power source base having a base connector and a light source is believed to be sold by Baxter, VH Mueller Division under the OPSIS (trademark). Milbank et al in U.S. Pat. No. 4,858,001 discloses modular endoscopic apparatus with image rotation. Jacoby in U.S. Pat. No. 5,230,621 discloses endoscopic method and device for subgingival dental procedure. Mushabac in U.S. Pat. No. 5,224,049 discloses method, system and mold assembly for use in preparing a dental prosthesis. Tsuji in U.S. Pat. No. 5,196,702 discloses photo-sensor and method for operating the same. Werly in U.S. Pat. No. 5,178,536 discloses dentistry set having a head inclined with respect to drill axis and using visual control. Oz in U.S. Pat. No. 5,079,629 discloses optical viewing device and system including same. Berg in U.S. Pat. No. 5,052,924 discloses fiberoptic imaging dental drill. Ademovic in U.S. Pat. No. 5,049,070 discloses dental drill integral camera and optics. Gandrud in U.S. Pat. No. 5,027,138 discloses dental camera system. Applegate et al in U.S. Pat. No. 5,016,643 discloses vascular entoptoscopy. Williams in U.S. Pat. No. 4,994,910 discloses modular endoscopic apparatus with probe. Gandrud in U.S. Pat. No. 4,987,433 discloses Ring and point strobe. Anapliotis in U.S. Pat. No. 4,974,580 discloses endoscope protective member. Duret et al in U.S. Pat. No. 4,952,149 discloses process and apparatus for taking a medical cast. Ogawa et al in U.S. Pat. No. 4,947,245 discloses image picking-up and processing apparatus. Lemmey in U.S. Pat. No. 4,915,626 discloses dental inspection and display apparatus. Brandestini et al in U.S. Pat. No. 4,837,732 discloses method and apparatus for the three-dimensional registration and display of prepared teeth. Baumrind et al in U.S. Pat. No. 4,836,778 discloses mandibular motion monitoring system. Halm et al in U.S. Pat. No. 4,829,548 discloses dental X-ray examination apparatus. Provost in U.S. Pat. No. 4,468,197 discloses apparatus and method for detecting cavities. Heitlinger et al in U.S. Pat. No. 4,324,546 discloses method for the manufacture of dentures and device for carrying out the method. Hamada et al in U.S. Pat. No. 4,234,306 discloses method and apparatus for sensing jaw position and movements and utilizing sensed data. Mullane in U.S. Pat. No. 4,184,175 discloses method of and apparatus for optically detecting anomalous subsurface structure in translucent articles. Russel U.S. Pat. No. 3,866,601 discloses a speculum in which a penetrating tube slidably receives a guide tube and is surrounded by a flexible sheath. Ibe U.S. Pat. No. 4,132,227 discloses an endoscope surrounded by a hollow cylindrical sheath extending toward but not to the distal end of the endoscope in order to create a fluid channel in the space between the sheath and the endoscope. Smith U.S. Pat. No. 4,201,199 discloses an endoscope surrounded by a rigid glass or plastic tube having an enlarged bulb at its distal end to space tissue away from the viewing window of the endoscope. The window is formed at an angle to provide viewing of a site offset from the axis of the endoscope. Yoon U.S. Pat. No. 4,254,762 discloses an endoscope surrounded by a sheath having a transparent lens at its distal end. The sheath may be at least partially open at its distal end for use with endoscopes having biopsy channels. Hampson U.S. Pat. No. 4,327,735 discloses a catheter surrounded by a transparent, collapsible sleeve through which the catheter projects at its distal end. Silverstein et al. U.S. Pat. No. 4,646,722 discloses another endoscope having a sterile flexible sheath which can be rolled up along the endoscope. A channel is provided between the endoscope and sheath through which biopsies can be taken. The sheath is not sealed at the upper end and will not maintain the sterility which is required within an operating room. D'Amelio U.S. Pat. No. 4,721,097 discloses another flexible sheath for use on an endoscope which has no seal at the upper end and does not provide the sterility required in an operating room. Sidall et al. U.S. Pat. No. 4,741,326 discloses a further flexible sheath which is rolled up along the endoscope and does not provide sterility or protection of the entire endoscopic device. U.S. Pat. Nos. 3,794,091 (Ersek et al), U.S. Pat. No. 3,809,072 (Ersek et al) and U.S. Pat. No. 4,772,275 (Erlich) are cited by Adair in U.S. Pat. No. 4,878,485 who discloses rigid video endoscope with heat sterilizable sheath. Saratoga U.S. Pat. No. 4,727,416 discloses electronic video dental camera. Saratoga U.S. Pat. No. 5,251,025 discloses electronic video dental camera. Nakamura et al U.S. Pat. No. 5,234,802 discloses method for processing a silver halide photographic material and light-sensitive material for photographing. Cooper et al U.S. Pat. No. 5,115,307 discloses electronic video dental camera. Lanza et al U.S. Pat. No. 5,090,040 discloses data acquisition system for radiographic imaging. Cooper et al U.S. Pat. No. 5,051,823 discloses dental instrument including laser device and electronic video dental camera. Cooper et al U.S. Pat. No. 5,016,098 discloses electronic video dental camera. Lanza et al U.S. Pat. No. 5,005,196 discloses limb positioning and calibration apparatus for radiographic imaging. Lanza et al U.S. Pat. No. 5,005,195 discloses digital readout system for radiographic imaging. Lanza et al U.S. Pat. No. 4,956,859 discloses source filter for radiographic imaging. Morris U.S. Pat. No. 4,797,101 discloses dental identification system. Cooper et al U.S. Pat. No. 4,757,381 discloses means and structure for prevention of cross contamination during use of dental camera. Brown British Patent No. 1,405,025 discloses a proctoscope surrounded by a concentric tube for providing a fluid channel.

The prior art does not provide a method of using a camera system having handpiece with a lens connected to a cable and a cable connector connected to the cable and at least two bases each having a base connector and a light source, wherein the cable connector is connected periodically to each of the base connectors.

The prior art does not provide a portable camera which includes a handpiece enclosed by a disposable sleeve and connected through a cable to a video processor in a cable connector adapted to be connected to a plurality of bases.

The prior art does not provide a method of sterile use of a portable dental camera by enclosing at least the distal end of the handpiece with a first sleeve, and generating an image of a first patient with the camera while it is connected to a first power source base in a first dental operatory room; replacing the first sleeve with a second sleeve, and generating an image of a second patient using the camera while it is connected to a second power source base in a second dental operatory room.

The prior art does not provide a dental handpiece having a handpiece housing, a charge coupled device (CCD) supported by the handpiece housing, a disposable sleeve enclosing at least a substantial portion of the handpiece housing, and a jacket holding the sleeve against the handpiece housing.

The prior art does not provide a dental handpiece having a handpiece housing, a charge coupled device (CCD) supported by the handpiece housing, a sterilizable reusable sleeve having a lens, and the sleeve enclosing at least a substantial portion of the handpiece housing, and a jacket holding the sleeve against the handpiece housing.

It is an object of the invention to provide a method of using a camera system having cable connected to a cable connector and a handpiece with a lens for periodic use with at least two bases each having a base connector a power source and a light source, wherein the cable connector is connected periodically to each of the base connectors.

It is an object of the invention to provide a portable camera which includes a handpiece enclosed by a disposable sleeve and connected through a cable to a video processor in a cable connector adapted to be connected to a plurality of bases each having a base connected, a power source and a light source.

It is an object of the invention to provide a method of sterile use of a portable dental camera by enclosing at least the distal end of the handpiece with a first sleeve, and generating an image of a first patient with the camera while it is connected to a first power source base in a first dental operatory room; replacing the first sleeve with a second sleeve, and generating an image of a second patient using the camera while it is connected to a second power source base in a second dental operatory room.

It is an object of the invention to provide a dental handpiece having a handpiece housing, a charge coupled device (CCD) supported by the handpiece housing, a disposable sleeve enclosing at least a substantial portion of the handpiece housing, and a jacket holding the sleeve against the handpiece housing.

It is an object of the invention to provide a dental handpiece having a handpiece housing, a charge coupled device (CCD) supported by the handpiece housing, a sterilizable reusable sleeve having a lens, and the sleeve enclosing at least a substantial portion of the handpiece housing, and a jacket holding the sleeve against the handpiece housing.

These problems of the prior art are overcome by the portable dental camera, system and method of the invention.

BRIEF DESCRIPTION OF THE INVENTION

Figure 1:
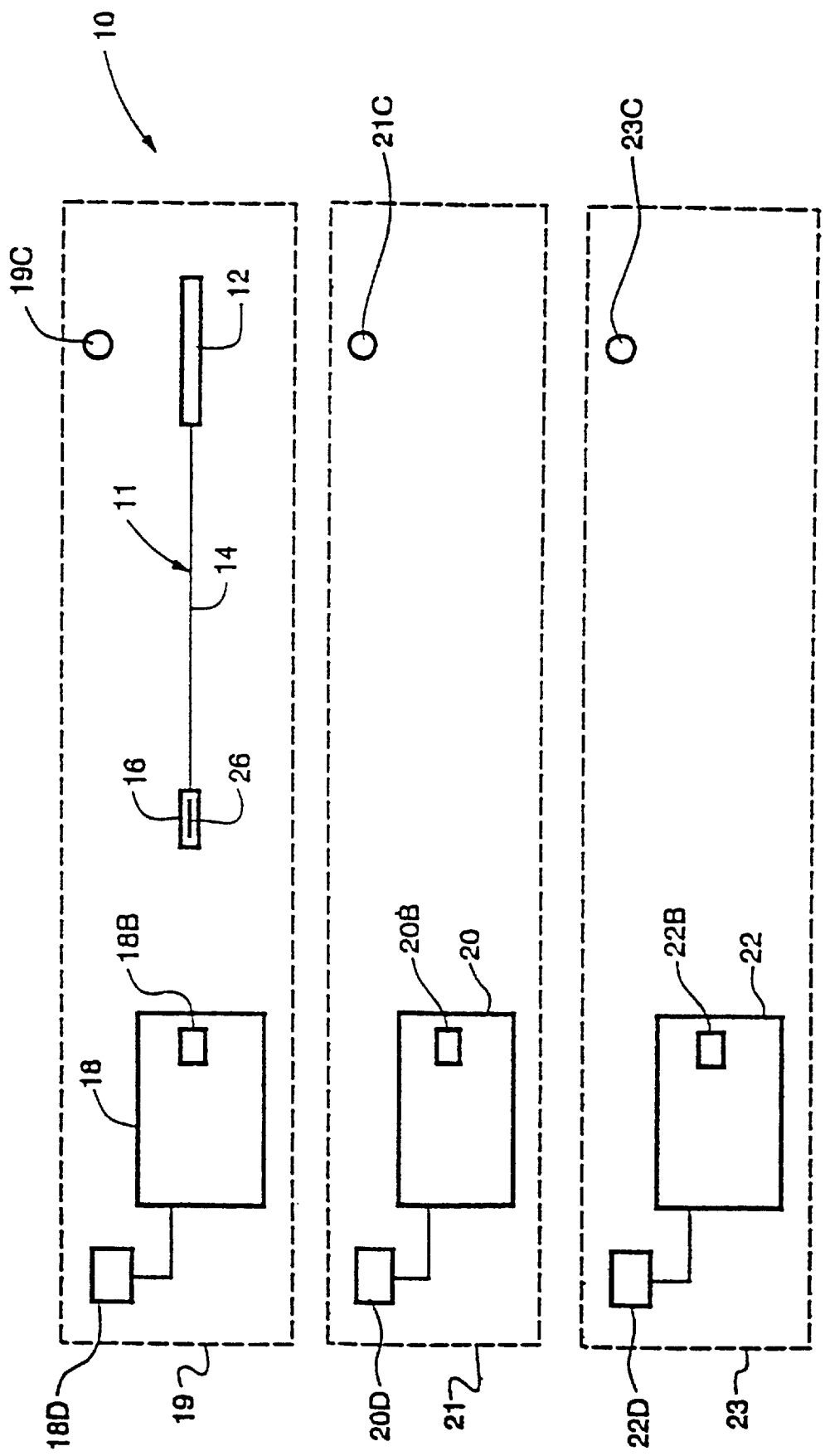
FIG. 1 is a schematic diagram of a camera system in accordance with the invention.
Figure 2:
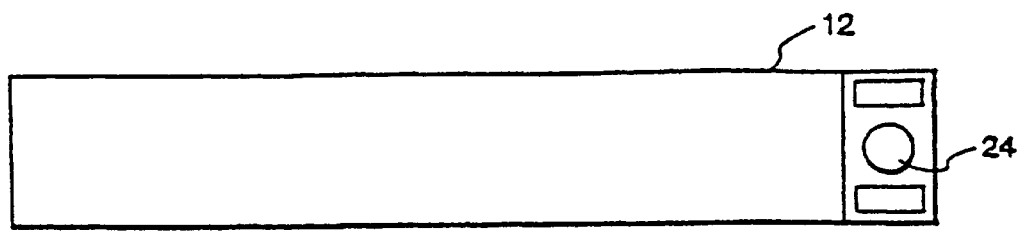
FIG. 2 is a schematic diagram of a camera handpiece for use in accordance with the invention.
Figure 3:
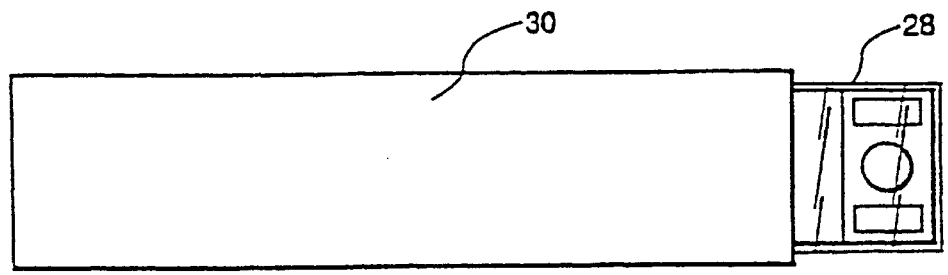
FIG. 3 is a schematic diagram of a lens sleeve holder positioned over a camera handpiece in accordance with the invention.
Figure 4:
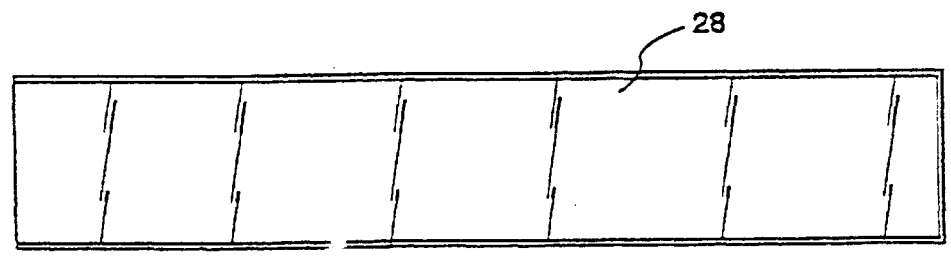
FIG. 4 is a schematic diagram of a sleeve for use with a camera handpiece in accordance with the invention.

The invention provides a camera system including a handpiece having a lens, and a cable connector connected to opposite ends of a cable and a plurality of power source bases. The cable connector includes a video processor. Each power source base has a base connector and a light source. The cable connector is adapted to be connected to each base connector. The camera system is used by connecting the cable connector one at a time to each of the base connectors. The handpiece is enclosed by a disposable sleeve. The sleeve is held against the handpiece by an autoclavable rigid jacket. The portable dental camera is maintained sterile by enclosing at least the distal end of the handpiece with a first sleeve, and generating an image of first patient with the camera and a first power source base in a first dental operatory room. The first sleeve is then removed from the handpiece and replaced with a second sleeve. An image of a second patient is then generated using the camera and a second power source base in a second dental operatory room. Preferably a sleeve which has a lens and is sterilizable and reusable is used to enclose the handpiece.

DETAILED DESCRIPTION OF THE INVENTION

The invention is now described with more particular reference to FIGS. 1–6 in which the same numeral refers to the same item throughout the drawings. Dental camera system 10 includes a portable dental camera 11 and a plurality of power source bases. Dental camera 11 includes handpiece 12, a cable 14 and a cable connector 16. Each of the power source bases 18, 20 and 22 is positioned separately in dental operatory rooms 19, 21 and 23 each having a motor actuated dental chair 19C, 21C or 23C respectively. Power source bases 18, 20 and 22 are connected independently by electrical conductors to displays 18D, 20D and 22D respectively. The handpiece 12 and cable connector 16 are supported at opposite ends of cable 14. Handpiece 12 supports lens 24. The handpiece 12 is generally elongated and cylindrical has a central axis. The lens 24 is portioned to receive light impinging on the handpiece in a direction substantially perpendicular normal to the central axis of the handpiece. Bases 18, 20 and 22 each have a base connector 18B, 20B and 22B and a light source. The cable connector 16 is adapted to be connected to each the base connectors 18B, 20B and 22B. The cable connector 16 includes a video processor 26. The camera system is used by connecting the cable connector one at a time to each of the base connectors. Disposable flexible sleeve 28 encloses at least the distal portion of the handpiece 12. Preferably the handpiece 12 is autoclavable. A rigid jacket 30 holds sleeve 38 against handpiece 12.

Figure 5:
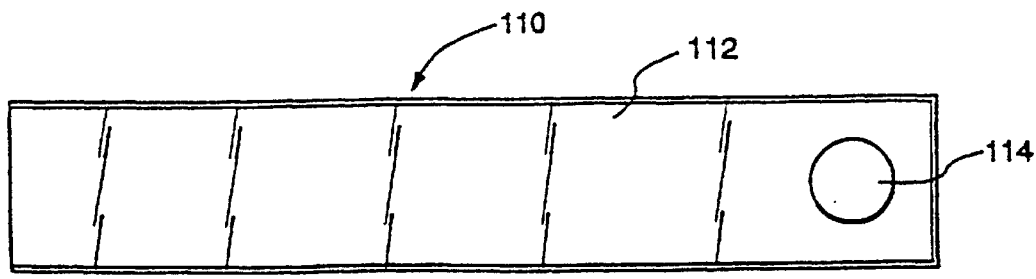
FIG. 5 is a schematic diagram of a sleeve having a lens for use with a camera handpiece in accordance with the invention.

With more particular reference to FIG. 5 it is seen that sterilizable, reusable cover 110 includes sleeve 112 and lens 114. Cover 110 is preferably positioned on handpiece 12 in place of sleeve 28. Cover 110 is positioned on handpiece 12 so that lens 114 is positioned over lens 24.

In a preferred embodiment of the invention lens 24 acts as a window and does not substantially refract light transmitted to the CCD of the dental handpiece enclosed by cover 110. In such embodiment of the invention the lens 114 of the cover 110 serves the purpose previously served by the lens (such as lens 24) of a handpiece. Thus, in such embodiment a transparent window is preferably substituted for the lens of the handpiece. Cover 110 is preferably used to cover a prior art dental handpiece having a CCD, such as the handpiece, disclosed by Milbank et al in U.S. Pat. No. 4,858,001. Preferably sleeve 112 is flexible, and when used to enclose a handpiece, a rigid jacket is preferably slid over sleeve 112 to hold it to the handpiece, in the manner that jacket 30 holds sleeve 28 to handpiece 12 in FIG. 3. Several covers having lenses of different focal lengths are preferably used one at a time to cover a dental handpiece.

Thus, cover 110 consists essentially of lens 114 and sleeve 112. Sleeve 112 is an elongated and generally cylindrical body wall. Lens 114 is supported by the body wall formed by sleeve 112.

Preferably, sleeve 112 is rigid and cover 110 is sterilizable. Preferably rigid sterilizable sleeves are made of metal or polymeric material. Preferably sleeve 112 is used in combination with a dental handpiece having a CCD. Cover 110 is positioned over the handpiece to substantially enclose the handpiece while lens 114 is positioned to refract light transmitted to the CCD.

Figure 6:
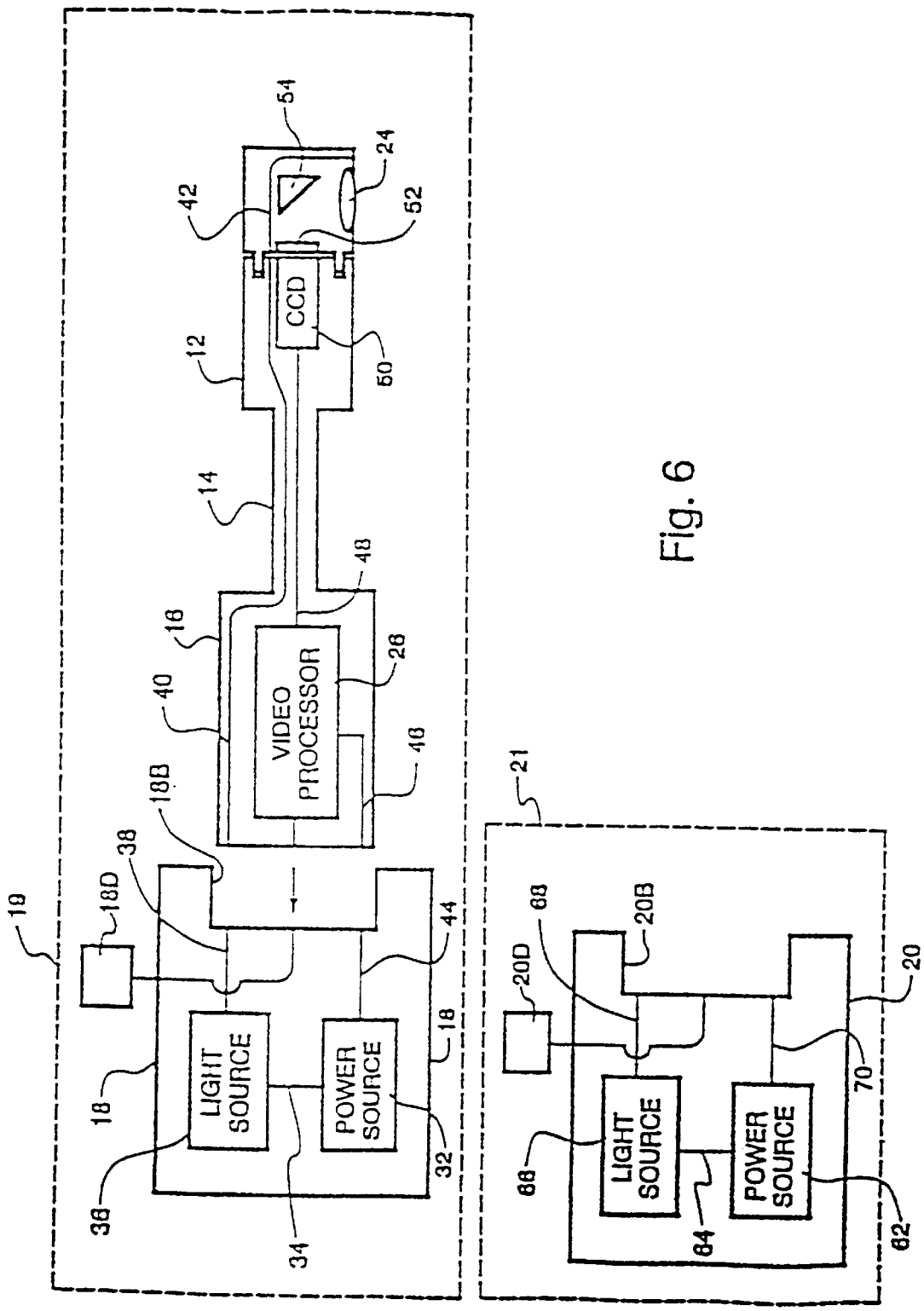
FIG. 6 is a schematic diagram of a camera system for use in a method in accordance with the invention.

With more particular reference to FIG. 6 it is seen that power source 32 is connected through electrical conductor line 34 to light source 36. Light source 36 is adapted to transmit light into optical fiber 38. Optical Fiber 38 is adapted to transmit light into optical fiber 40 when cable connector 16 is fully inserted into base connector 18B. Optical fiber 40 is adapted to transmit light into optical fiber 42 which emits light from handpiece 12. Power source 32 is connected to electrical conductor 44. Electrical conductor 44 is adapted to be connected to electrical conductor 46 when cable connector 16 is fully inserted into base connector 18B. Electrical conductor 46 is connected to video processor 26. Video processor 26 is connected through electrical conductor 48 to charge coupled device (CCD) 50. Charge coupled device (CCD) 50 is supported within handpiece 12 in a position whereby light is transmitted thereto from lens 24 upon reflection from prism 54 through window 52. Power source 62 is connected through electrical conductor 64 to light source 66. Light source 66 is connected to optical fiber 68. Power source 62 is connected to electrical conductor 70.

In a preferred embodiment of the invention the handpiece is autoclavable. However, the use of an autoclavable handpiece is not necessary to practice a preferred method of the invention.

Preferably the camera is completely portable. Readily detachable lenses preferably include lenses for intra oral use and lenses for extra oral use. Intra oral lenses preferably include a magnifying lens a close focus lens and/or an intra oral lens. An extra oral lens preferably is provided with an adjustable focus and an adjustable f-stop. Preferably the housing for the power supply and light source is supported on a countertop or on a post in a dental operatory room. Preferably the power supply and light source are operated by a foot control switch. Preferably this foot control switch has freeze frame capability, for example by use of the memory of a color printer. Preferably a single color printer is connected to a plurality of light sources, monitors, foot controls, and/or character generators. Character generation capability is preferred. Any number of operatories having a power source base and display are serviced by a single handpiece system in accordance with the invention. Preferably each of the power source bases are connected to a color printer, video cassette recorder and disk recorder located in a central location. Preferably, each foot control activates recorder(s) and/or printer(s) for freeze control and printing. Thus, only one printer and one recorder are required for a single dental office having a plurality of operatory rooms.

Preferably portable dental cameras in accordance with the invention are readily detachable to allow sterilization thereof and/or have a barrier sleeve to provide a barrier to contamination thereof. Preferably at least the distal end of the handpiece is enclosed by a removable slip on sleeve which makes it unnecessary to change the handpiece, only the sleeve, between use with different patients. Removal of the sleeve allows a difference lens to be attached before a new sleeve is slid over the handpiece. Jackets preferably are capable of withstanding autoclaving, chemiclaving and/or dry heat sterilizating. Jackets preferably have a useful life of at least 1,000 sterilization cycles.

Preferably, the sleeve is made of an optically transparent material. In a preferred embodiment of the invention the sleeve includes a lens which is positioned adjacent to a window in the handpiece. Preferably the sleeve and its lens are sterilizable and reusable.

In a preferred embodiment of the invention a removable barrier sleeve encloses a handpiece having a magnification lens. Barrier sleeves are preferably optically clear so as not to distort image resolution, while being of sufficiently low cost to be completely disposable.

In a preferred embodiment of the invention the handpiece including lens, video, processor and cable are sterilizable as a contiguous unit. The preference is for steam, gas, pressure and/or temperature sterilizability. However, sterilization and/or disinfection of the handpiece is alternatively carry out by immersion in gluteraldehydes, quarternary ammonium compounds, iodophors, phenols and sodium hypochlorite in concentrations of from about 5 to about 15 percent (5–15%).

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of using a dental camera system, comprising;
providing a camera system comprising a handpiece having a lens, charged coupled device (CCD), a cable, a cable connector and a first and a second power source base, said handpiece being supported by said cable, said cable connector being supported by said cable, said cable connector comprising a video processor, each said power source base having a base connector and a light source, said cable connector being adapted to be connected to each said power source base connector,
connecting said cable connector to said first base connector,
removing said cable connector from said first base connector then connecting said cable connector to said second base connector,
then removing said cable connector from said second base connector, and then reconnecting said cable connector to said first base connector.

2. The method of claim 1 wherein said handpiece comprises a handpiece housing and a lens housing and said lens housing is releasably connected to said handpiece housing.

3. The method of claim 1 wherein said handpiece has a distal end, and at least the distal end of said handpiece is enclosed by a sleeve.

4. The method of claim 3 wherein said sleeve has a proximal end, and the proximal end of said sleeve is enclosed by a autoclavable jacket.

5. The method of claim 1 wherein each power source base is in a separate dental operatory room, each said room having a motor actuated chair.

6. The method of claim 1 wherein said handpiece further comprises a prism.

7. A dental camera system, comprising:

a handpiece, a cable, a cable connector, and a plurality of dental operatory rooms each having a power source base, said handpiece having a lens and a prism, said handpiece being supported by said cable, said cable connector being supported by said cable, each said power source base having a base connector and a light source, said cable connector being adapted to be connected to each said base connector.

8. The dental camera system of claim 7 wherein said cable connector comprises a video processor.

9. The dental camera system of claim 7 wherein said handpiece comprises a handpiece housing and a lens housing and said lens housing is a readily releasable from said handpiece housing.

10. The dental camera system of claim 7 wherein at least the distal end of said handpiece is enclosed by a sleeve.

11. The dental camera system of claim 10 wherein the proximal end of said sleeve is enclosed by a autoclavable jacket.

12. The dental camera system of claim 7 wherein each dental operatory room has a motor actuated chair.

* * * * *